US009955972B1

United States Patent
Buelna (10) Patent No.: US 9,955,972 B1
(45) Date of Patent: *May 1, 2018

(54) SYSTEMS AND METHODS FOR CREATING ARTERIOVENOUS (AV) FISTULAS

(71) Applicant: Avenu Medical, Inc., San Juan Capistrano, CA (US)

(72) Inventor: Terry Buelna, Montecito, CA (US)

(73) Assignee: AVENU MEDICAL, INC., San Juan Capistrano, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/582,412

(22) Filed: Apr. 28, 2017

Related U.S. Application Data (60) Continuation of application No. 14/831,700, filed on Aug. 20, 2015, now Pat. No. 9,649,157, which is a
(Continued)

(51) Int. Cl.
| | |
|---|---|
| *A61B 17/17* | (2006.01) |
| *A61B 17/11* | (2006.01) |
| *A61B 18/14* | (2006.01) |
| *A61B 17/00* | (2006.01) |
| *A61B 18/00* | (2006.01) |

(52) U.S. Cl.
CPC .......... *A61B 17/11* (2013.01); *A61B 18/1492* (2013.01); *A61B 2017/00986* (2013.01); *A61B 2017/1107* (2013.01); *A61B 2017/1139* (2013.01); *A61B 2018/00279* (2013.01); *A61B 2018/00404* (2013.01); *A61B 2018/00595* (2013.01); *A61B 2018/00601* (2013.01);
(Continued)

(58) Field of Classification Search
CPC ...... A61B 18/1445; A61B 2018/00601; A61B 2018/1455; A61B 2018/0063; A61B 18/1402; A61B 18/14; A61B 2018/00607; A61B 18/18; A61B 2018/1475
See application file for complete search history.

(56) References Cited

U.S. PATENT DOCUMENTS

| | | |
|---|---|---|
| 5,290,278 A | 3/1994 | Anderson |
| 5,425,731 A | 6/1995 | Daniel et al. |
| (Continued) | | |

*Primary Examiner* — Rex R Holmes
(74) *Attorney, Agent, or Firm* — Donald E. Stout; Stout, Uxa & Buyan, LLP (57) ABSTRACT

A method of creating an AV fistula between adjacent first and second blood vessels, includes steps of cutting a hole through the adjacent walls of the first and second blood vessels and inserting a welding catheter into the first vessel, and through the hole into the second vessel, so that a distal end of the welding catheter is disposed within the second vessel. A portion of wall defining the welding catheter is then expanded radially outwardly, and the expanded wall portion is pulled proximally to engage the wall of the second blood vessel and to pull it toward the wall of the first blood vessel. Then, a portion of wall proximal to the first expanded wall portion and disposed in the first blood vessel is expanded radially outwardly, thereby capturing the walls of each of the second and first blood vessels between the two expanded wall portions. Cutting elements on the expanded wall portions are then energized to create a tissue welded elongate aperture between the first and second blood vessels.

16 Claims, 10 Drawing Sheets

Related U.S. Application Data division of application No. 13/458,629, filed on Apr. 27, 2012, now Pat. No. 9,138,230.

(60) Provisional application No. 61/480,638, filed on Apr. 29, 2011.

(52) U.S. Cl.
CPC ............... *A61B 2018/00619* (2013.01); *A61B 2018/1425* (2013.01)

(56) References Cited

U.S. PATENT DOCUMENTS

| | | | |
|---|---|---|---|
| 5,830,222 A | 11/1998 | Makower | |
| 5,830,224 A | 11/1998 | Cohn et al. | |
| 6,068,637 A | 5/2000 | Popov et al. | |
| 6,068,638 A | 5/2000 | Makower | |
| 6,071,292 A | 6/2000 | Makower et al. | |
| 6,083,223 A | 6/2000 | Baker | |
| 6,099,542 A | 8/2000 | Cohn et al. | |
| 6,190,353 B1 | 2/2001 | Makower et al. | |
| 6,235,027 B1 | 5/2001 | Herzon | |
| 6,283,983 B1 | 9/2001 | Makower et al. | |
| 6,302,875 B1 | 10/2001 | Makower et al. | |
| 6,330,884 B1 | 12/2001 | Kim | |
| 6,375,615 B1 | 4/2002 | Flaherty et al. | |
| 6,379,319 B1 | 4/2002 | Garibotto et al. | |
| 6,398,797 B2 | 6/2002 | Bombard et al. | |
| 6,464,665 B1 | 10/2002 | Heuser | |
| 6,533,778 B2 | 3/2003 | Herzon | |
| 6,561,998 B1 | 5/2003 | Roth et al. | |
| 6,579,311 B1 | 6/2003 | Makower | |
| 6,613,081 B2 | 9/2003 | Kim et al. | |
| 6,616,675 B1 | 9/2003 | Evard et al. | |
| 6,669,709 B1 | 12/2003 | Cohn et al. | |
| 6,699,245 B2 | 3/2004 | Dinger et al. | |
| 6,709,444 B1 | 3/2004 | Makower | |
| 6,726,677 B1 | 4/2004 | Flaherty et al. | |
| 6,863,684 B2 | 3/2005 | Kim et al. | |
| 6,908,463 B2 | 6/2005 | Treat et al. | |
| 6,929,009 B2 | 8/2005 | Makower et al. | |
| 7,056,325 B1 | 6/2006 | Makower et al. | |
| 7,159,592 B1 | 1/2007 | Makower et al. | |
| 7,191,015 B2 | 3/2007 | Lamson et al. | |
| 7,316,655 B2 | 1/2008 | Garibotto et al. | |
| 7,351,247 B2 | 4/2008 | Kupiecki et al. | |
| 7,387,636 B2 | 6/2008 | Cohn et al. | |
| 7,588,566 B2 | 9/2009 | Treat et al. | |
| 7,729,738 B2 | 6/2010 | Flaherty et al. | |
| 7,846,172 B2 | 12/2010 | Makower | |
| 2006/0111704 A1* | 5/2006 | Brenneman | A61B 17/11 606/41 |
| 2006/0142788 A1 | 6/2006 | Wilson et al. | |
| 2011/0230897 A1* | 9/2011 | Palermo | A61B 17/0057 606/142 |

\* cited by examiner

SYSTEMS AND METHODS FOR CREATING ARTERIOVENOUS (AV) FISTULAS

This application is a continuation under 35 U.S.C. 120 of U.S. application Ser. No. 14/831,700, entitled Systems and Methods for Creating Arteriovenous (AV) Fistulas, filed on Aug. 20, 2015, now allowed, which in turn is a divisional under 35 U.S.C. 120 of U.S. application Ser. No. 13/458,629, filed on Apr. 27, 2012, entitled Systems and Methods for Creating Arteriovenous (AV) Fistulas, now U.S. Pat. No. 9,138,230, which in turn claims the benefit under 35 U.S.C. 119(e) of the filing date of Provisional U.S. Application Ser. No. 61/480,638, entitled Systems and Methods for Creating Arteriovenous (AV) Fistulas, filed on Apr. 29, 2011. All of the foregoing applications are expressly incorporated herein by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact, and to create a leak-free blood flow path between them. The vessels are joined together with suture or clips, in an open surgical procedure. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser, and a number of methods using various connecting prosthesis, clips, and stents. Such procedures are time consuming, clinician dependent (open to surgical error), and often result in strictures, or clotting of the vein or artery.

An arterio-venous fistula (AVF) is created by connecting an artery to a vein. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with catheters placed in large veins, prosthetic grafts attached to an artery and a vein, or a fistula where an artery is attached directly to the vein.

Fistulas for hemodialysis are required by patients with kidney failure. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater. Dialysis fistulas have to be close to the skin (<6 mm), and large enough (>4 mm) to access with a large needle. The fistula needs to be long enough (>6 cm) to allow adequate separation of the access and return needle to prevent recirculation of dialysed and non-dialysed blood between the needles inserted in the fistula.

To create a fistula, it is necessary to carefully dissect an artery and vein from their surrounding tissue, and to join them to create a leak-free blood flow path between them. This is typically done by suturing the vein to the artery in an open surgical procedure, using fine suture or clips. The vein is either attached by an end to end anastomosis, end to side anastomosis, or a side to side anastomosis. The procedure is time consuming, clinician dependent (open to surgical error), and often times results in strictures, or clotting of the vein or artery. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

The present disclosed invention eliminates the above described open procedures, reduces operating time, and allows for a consistent and repeatable fistula creation.

It is well known that heat, whether its source is Radio Frequency (RF), resistance, or laser, will attach and weld tissue or vessels upon direct pressure and contact over the targeted weld area. This is often done with jaw-type, compression heat delivery devices. It is also well known that radially expandable devices such as balloons, metal cages, and baskets are often coupled with energy in the form of RF, or in the case of balloons, heated saline, and used intraluminally to ablate tissue, stop bleeding, or create a stricture.

The present invention uses two pair of opposable, collapsible slits on the main catheter body that extend outwards and trap with compression the surrounding vessel walls between them. Heat is then applied to the tissue using RF energy or resistance heat through the exposed woven wire elements. The woven wire elements are actually a component of the coaxial wire mesh embedded into the main catheter body. This coaxial mesh serves two purposes. One is to increase the torqueability of the main catheter, and a second is to supply energy to the exposed electrodes. The electrodes are created by scathing a desired amount of the encapsulating layer of polymer over the wire mesh. Heat from the device travels internally through the vessel walls to the adventitia which surrounds the vessels. With the combination of heat and clamping force, the vessels are joined together.

More particularly, there is provided a device for creating an arteriovenous (AV) fistula, which comprises a welding catheter comprising an elongate tube having a circumferential wall. The first portion of the wall is actuatable between a collapsed orientation wherein the distal portion is axially aligned with remaining portions of the circumferential wall and a radially expanded orientation. A second portion of the wall, spaced proximally from the first wall portion, is actuatable between a collapsed orientation wherein the distal portion is axially aligned with remaining portions of the circumferential wall and a radially expanded orientation. Tissue cutters are disposed on the circumferential wall on and adjacent to the first and second portions thereof. The first wall portion further comprises a plurality of circumferentially spaced slots disposed therein, which in one embodiment comprises a pair of circumferentially opposed slots. The second wall portion also comprises a plurality of circumferentially spaced slots disposed therein, which in one embodiment also comprises a pair of circumferentially opposed slots.

The first and second portions of the wall are each biased toward their respective radially expanded orientations. The elongate tube further comprises an axial through hole and an inner tube disposed in the axial through hole, wherein the elongate tube and the inner tube are attached to one another distally of the first and second wall portions. An actuator is disposed on a handle proximal to the elongate tube, for actuating the first and second wall portions between their radially expanded and collapsed orientations. The actuator has a first position for radially expanding only the first portion of the wall and a second portion for also radially expanding the second portion of the wall. In the disclosed embodiments, the actuator functions to actuated the radially expanding first and second portions by pulling the inner tube proximally.

An outer sheath is axially positionable to cover both of the radially expanding first and second wall portions, and is alternatively axially positionable to selectively expose only the first wall portion or both of the first and second wall portions.

A power source is provided for selectively energizing the tissue cutters, which, in certain embodiments, are energized by RF energy. In the illustrated embodiments, the tissue cutters comprise wire mesh electrodes.

In another aspect of the invention, there is disclosed a method of creating an AV fistula between adjacent first and second blood vessels, which comprises steps of cutting a hole through the adjacent walls of the first and second blood vessels and inserting a welding catheter into the first vessel, and through the hole into the second vessel, so that a distal end of the welding catheter is disposed within the second vessel. A portion of wall defining the welding catheter is then expanded radially outwardly, and the expanded wall portion is pulled proximally to engage the wall of the second blood vessel and to pull it toward the wall of the first blood vessel. Then, a portion of wall proximal to the first expanded wall portion and disposed in the first blood vessel is expanded radially outwardly, thereby capturing the walls of each of the second and first blood vessels between the two expanded wall portions. Cutting elements on the expanded wall portions are then energized to create a tissue welded elongate aperture between the first and second blood vessels.

An additional method step following the foregoing steps involves collapsing the first and second expanded wall portions and withdrawing the welding catheter from the blood vessels. The energizing step, in certain embodiments, comprises energizing electrodes, which may comprise wire mesh electrodes, with RF energy.

The hole cutting step may be performed, in accordance with the inventive method, by inserting a needle into the first blood vessel, extending an obturator through a lumen in the needle until a tip thereof contacts the wall of the first blood vessel, and energizing a cutting tip of the obturator to cut the hole.

Preferably, an outer sheath is disposed over an elongate tube comprising the welding catheter, and the inventive method further comprises a step of withdrawing the outer sheath proximally to expose the first wall portion prior to the first expanding step. The method further comprises a step of withdrawing the outer sheath proximally to expose the second wall portion prior to the second expanding step.

The invention, together with additional features and advantages thereof, may best be understood by reference to the following description taken in conjunction with the accompanying illustrative drawings.

DESCRIPTION OF THE PREFERRED EMBODIMENT

Referring now particularly to FIGS. 19-22, a particular embodiment of a system for creating an A-V fistula, in accordance with the principles of the present invention, will be described. A welding catheter 10 (FIG. 20) comprises, in a presently preferred embodiment, a 3-4f (French) (70-80 shore A) elongate tube or outer sheath 12, having a through hole 14 for accommodating a 2-3f inner tube 16 and a standard 0.014 diameter guidewire. A distal end 18 is tapered with a softer (40-50 shoreA) polymer tip which is in the range of 1-2 inches in length. This is to allow atraumatic ease of entry into and through the vessels. The inner tube 16 is preferably constructed of a flexible material such as a polymer in the range of 70-90 shoreA or a thin-walled nitinol metal. The distal end of the main catheter tube 12 features four (4) slots 20, 20a.

The slots 20, 20a are arranged so that there are two slots 20, 20a in series on each side of the tube 12, with each set of two slots 20, 20a opposed 180 degrees from one another about the circumference of the tube. Thus, there is a set of distal opposed slots 20, and a second set of proximal opposed slots 20a. The slots 20, 20a are preferably within a range of 0.030-0.060 inches long, and are biased to be axially collapsed, as shown in FIG. 20, when tension is applied to the inner tube 16. The inner tube 16 must have enough column strength to activate the collapsible wings (described below) into their radially expanded orientation when it is pulled proximally. To clarify terminology used throughout this application, when the slots are axially collapsed, the wings are radially expanded. Likewise, when the slots are axially expanded, the wings are radially collapsed. The inner 3f tube 16 is attached to the inner diameter (ID) of the outer 4f tube 12 near the distal end. A 4-5f elongate tube 22 extends over the tube 12 and is slidably attached at the proximal end thereof. The outer tube 12 is attached to a handle 24 at a proximal end 26, and is fixed in place. Wire mesh 28 of the outer tube 12 is exposed, as shown, and a conductor wire 30, preferably in a range of 16-20 Ga. (Gauge) is attached to the mesh, as shown, at one end, and has a standard banana connector 32 at the opposite end for attachment to an RF generator. The inner tube 16 is attached at the distal end by the slidable actuator handle 24. The actuator handle 24 has two positions. A first position 31a (FIG. 20), actuates the axial collapse of the distal set of slots 20, so that first radially protruding wings 34 are formed by expanding radially outwardly, as shown in FIG. 20a. A second position 31b (FIG. 20), actuates the further collapse of the proximal set of slots 20a, as shown in FIG. 20b, to form second radially protruding wings 36, proximally of the first wings 34. These two sets of wings 34, 36, when the slots 20, 20a are collapsed, have an expanded width of approximately 3-6 mm. The inner tube 16 has a through lumen 38 to allow passage over a guidewire.

Figure 19:
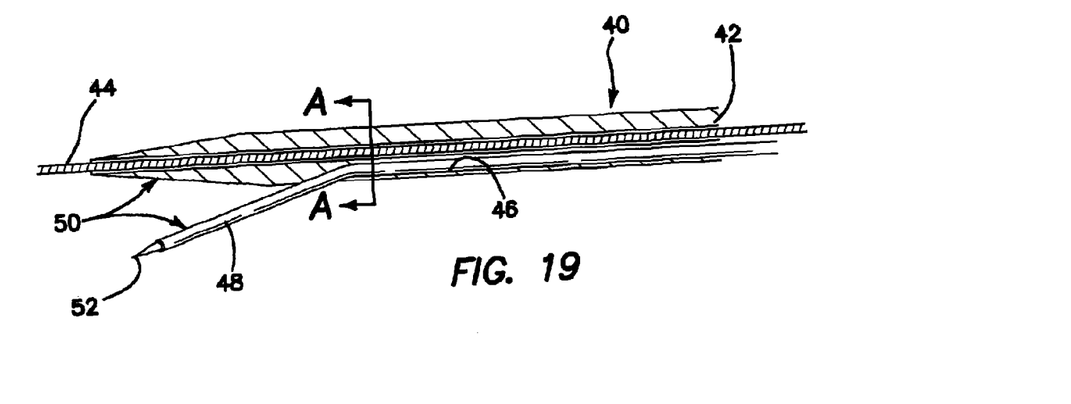
FIG. 19 is a cross-sectional view of a multilumen catheter and associated structure.
Figure 19A:
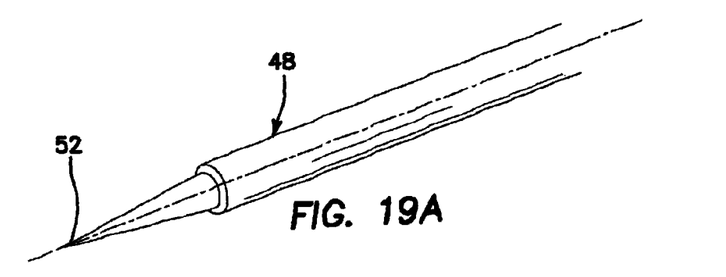
FIGS. 19a-19c illustrate alternative distal work pieces for the needle and associated cutting features of the inventive system.
Figures 19B, 19C:
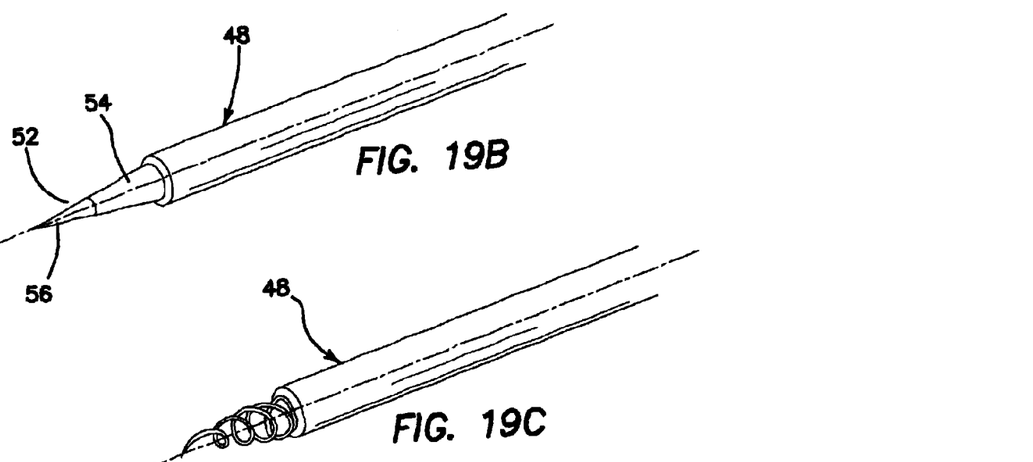
Figures 19D, 20, 20A, 20B:
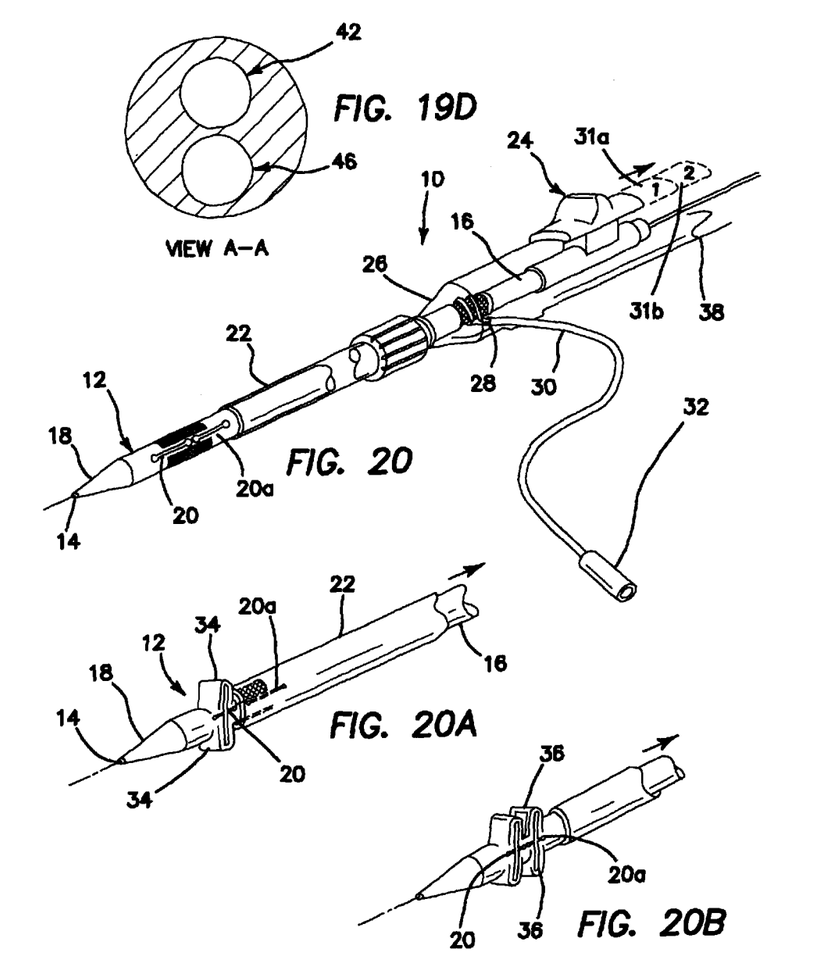
FIG. 19d is a cross-sectional view taken through lines A-A of FIG. 19.
FIG. 20 is an isometric view of a welding catheter constructed in accordance with the principles of the present invention.
FIGS. 20a and 20b illustrate a distal portion of the welding catheter of FIG. 20 in sequential modes.

Now referring particularly to FIGS. 19, 19a, 19b, and 19c, there is shown a multilumen catheter 40, preferably having a 4-5f diameter. A central lumen 42 accommodates the passage of a standard 0.018 diameter guidewire 44. A second lumen 46 accommodates a pre-bent cannulated needle 48, having a 0.015 inside diameter to accommodate a 0.014 diameter guidewire. The angle 50 of the bent needle 48 is preferably within the range of 30-45 degrees, and includes a removable pencil point tip obturator 52. The obturator 52 is fabricated of nitinol or other suitable material, and insulated 54, as shown in FIG. 19b, with only the tip 56 exposed. Heat is applied to the tip 56 from an RF energy source connected to the distal end. The catheter 40 is preferably made of a polymer in the range of 60-75 shoreA. The needle 48 is preferably made of nitinol, with an OD in the range of 0.019-0.021. The memory characteristics of nitinol allow the needle to deform and nest while in the catheter lumen. The distal end of the catheter is tapered to allow ease of entry into the vessel. FIGS. 19a, 19b, and 19c show alternative obturator designs. FIG. 19b is the presently preferred embodiment, already discussed above, while FIG. 19a shows a cold tip without RF heat, and FIG. 19c shows a corkscrew or auger design which allows traction during penetration into the vessel. The guidewire 44 can be run through the corkscrew device.

Figure 1:
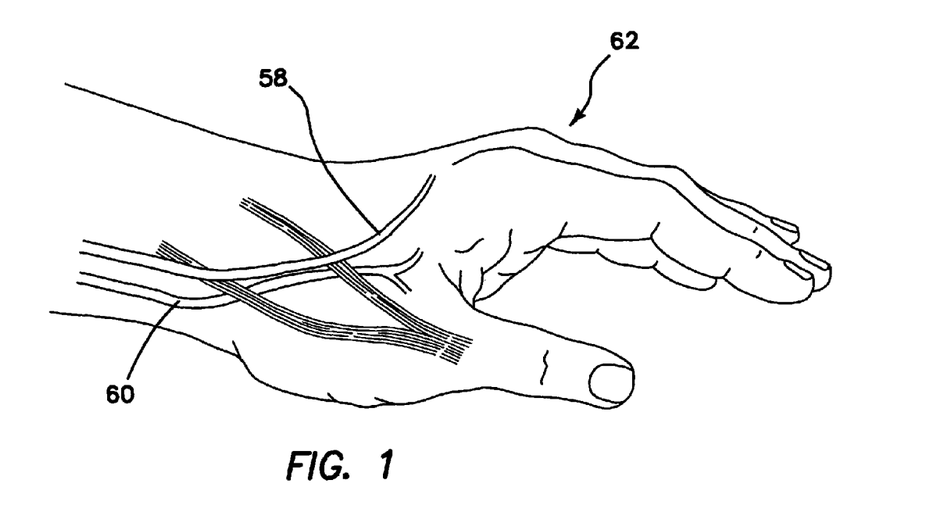
FIG. 1 is an isometric view showing the first step of an inventive method for creating an A-V fistula in accordance with the principles of the present invention.
Figure 2:
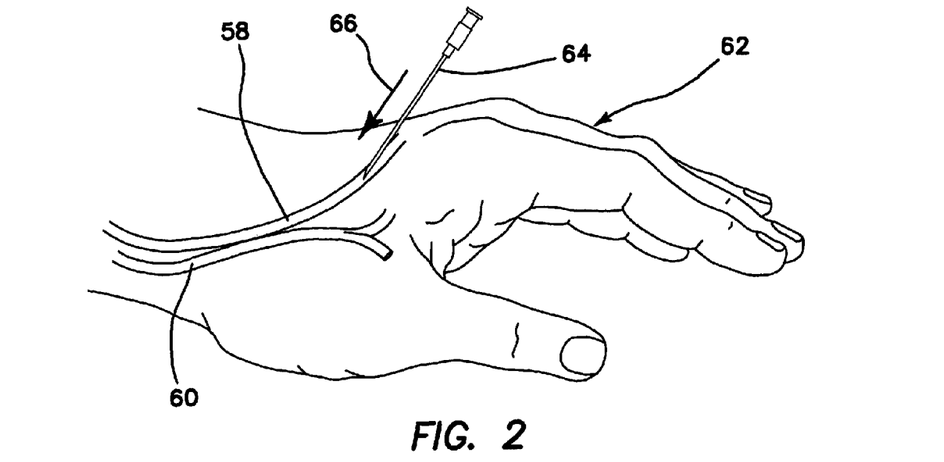
FIG. 2 is a view similar to FIG. 1, wherein a needle has been inserted into a vessel in the hand of a patient.
Figure 3:
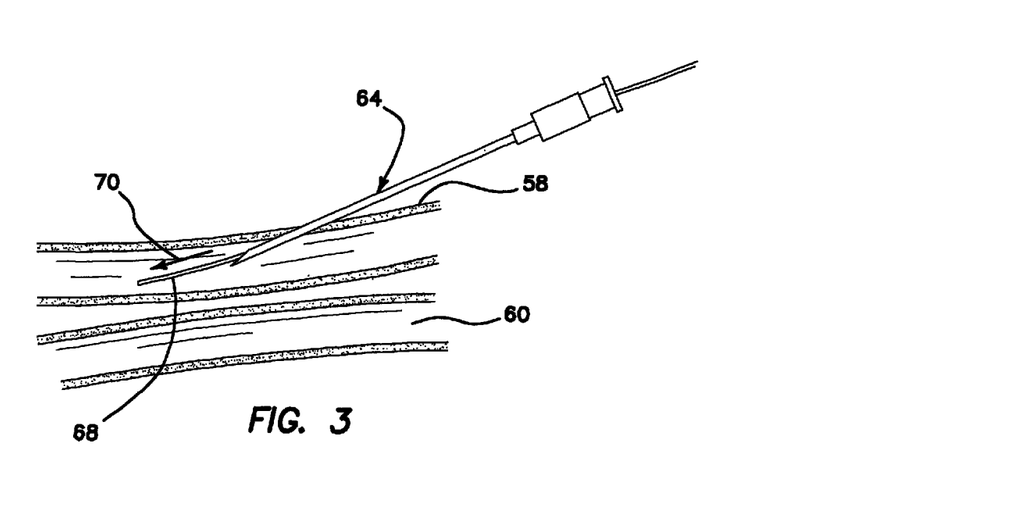
FIG. 3 is a view illustrating the insertion of a guidewire through the needle into the vessel.
Figure 4:
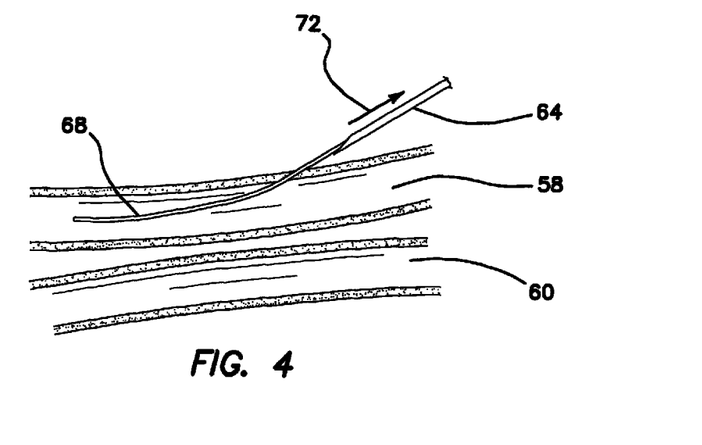
FIG. 4 is a view similar to FIG. 3 wherein the needle has been withdrawn and removed.

With particular reference now to FIGS. 1-18, to begin the inventive method of creating an AV fistula, the practitioner selects an appropriate procedural site having each of a first vessel 58 and a second vessel 60 in close proximity to one another. In currently preferred approaches, the first vessel 58 comprises a vein, and the second vessel 60 comprises an artery, but the invention is not necessarily limited to this arrangement. As illustrated in FIG. 1, one presently preferred location is the hand 62 of a patient. Then, generally employing principles of the Seldinger technique, as shown in FIG. 2, the first vessel 58 is punctured by a needle 64, which is inserted therein, in the direction of an arrow 66. A first guidewire 68, preferably a standard 0.014 diameter guidewire, is then inserted through a lumen of the hollow needle 64 into the vessel 58, and advanced in the direction of an arrow 70 (FIG. 3). Following this, as shown in FIG. 4, the needle 64 is removed, by withdrawing it in the direction of an arrow 72.

Figure 5:
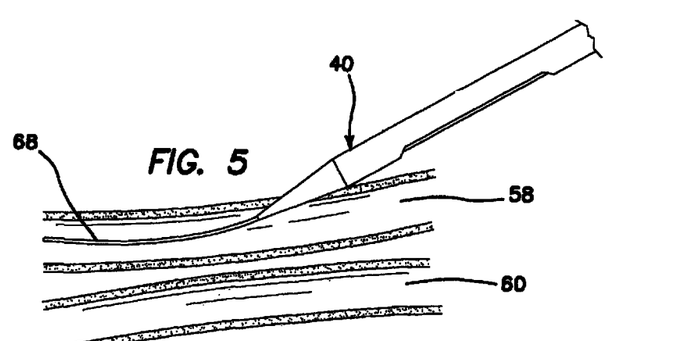
FIGS. 5-18 are sequential views illustrating one method of utilizing the inventive system.
Figures 6, 7:
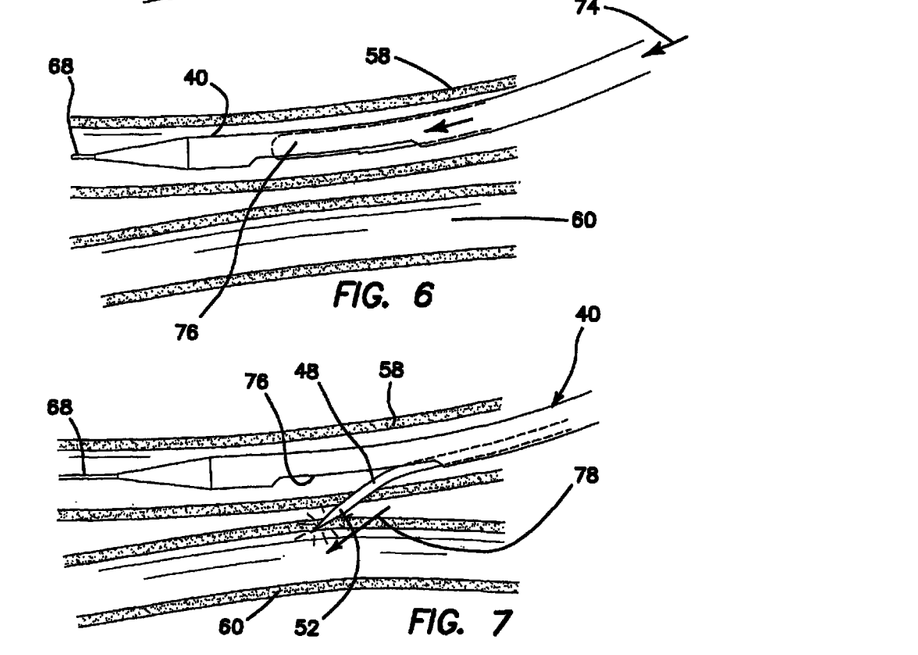
Figure 8:
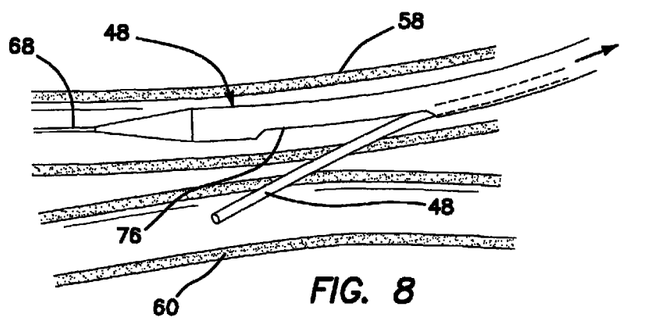
Figure 9:
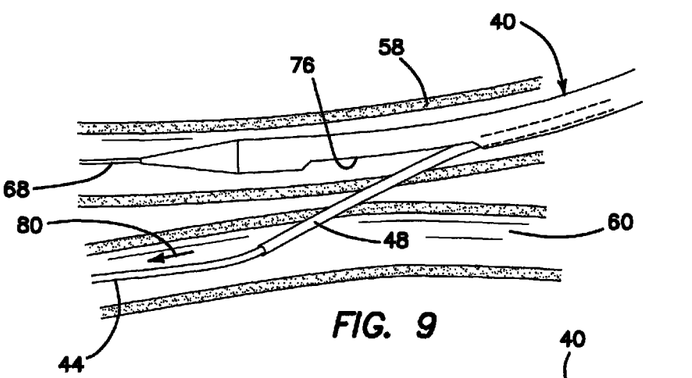
Figure 10:
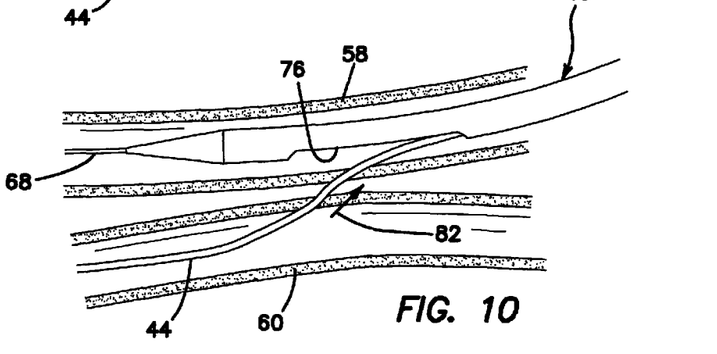
Figure 11:
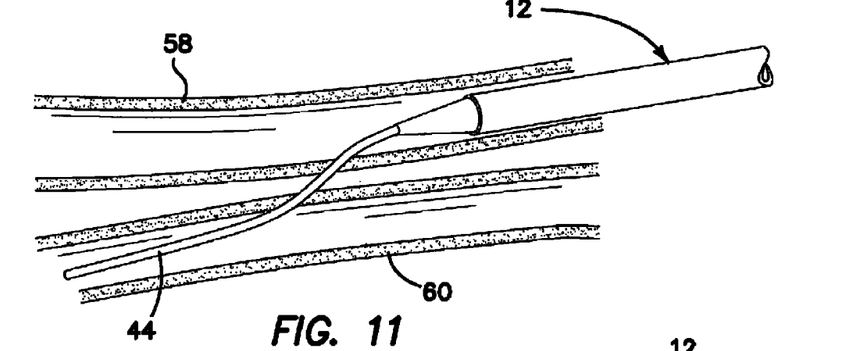
Figure 12:
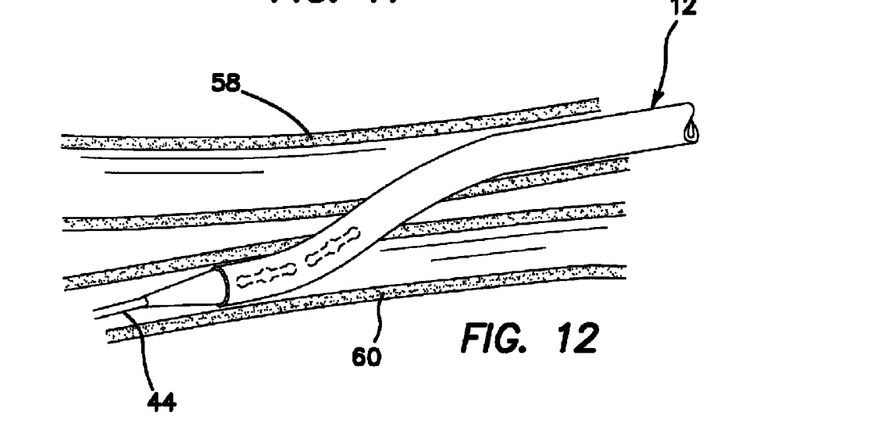

The vessel access catheter 40 is placed over the first guidewire 68 and inserted over the guidewire into the first vessel 58, in the direction of arrow 74, as shown in FIG. 5. As illustrated in FIG. 6, the pre-bent cannulated needle 48 is then extended out of the catheter 40 from a side port 76 and into contact with the second vessel 60. The obturator (FIG. 19) 52, with its cutting tip is extended through the needle 48, and RF energy is applied to the needle, as shown in FIG. 7, preferably in the range of 10-20 W monopolar, creating a hole in the vessel walls and allowing the needle 48 to extend in the direction of arrow 78 farther into the second vessel 60. Then, as shown in FIG. 8, the obturator cutting element 52 is removed, and the second guidewire 44 is passed through the lumen of the needle 48, distally in the direction of arrow 80 (FIG. 9). This second guidewire 44 creates the access path for the welding catheter 10 (FIG. 20). The access needle 48 is retracted in the direction of arrow 82 (FIG. 10), and the welding catheter 12 is passed over the guidewire 44 distally into the first vessel, and then into the second vessel, as shown in FIGS. 11 and 12.

Figure 13:
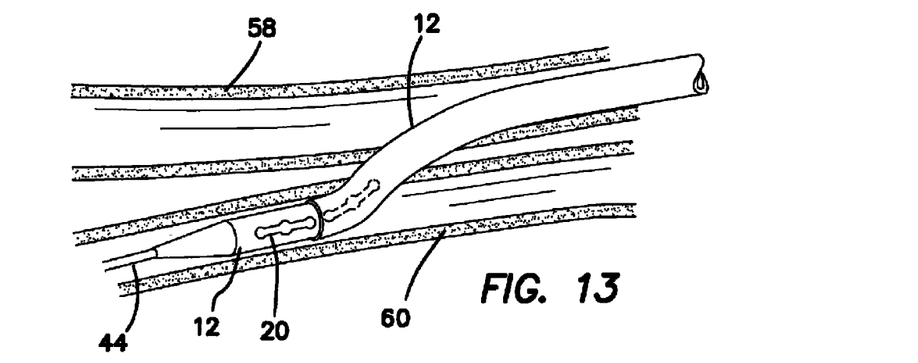
Figure 14:
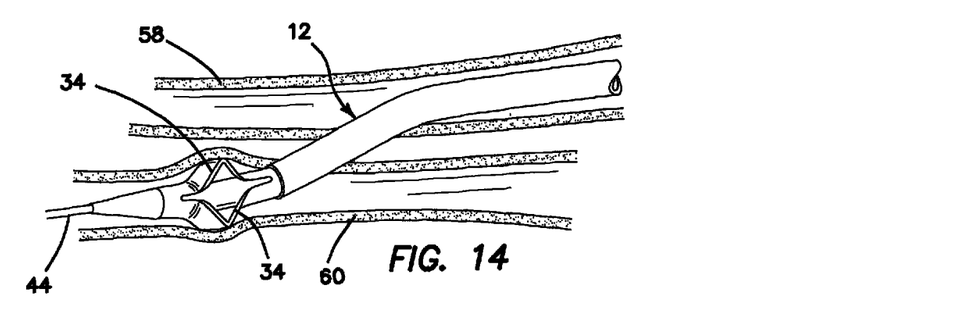
Figure 15:
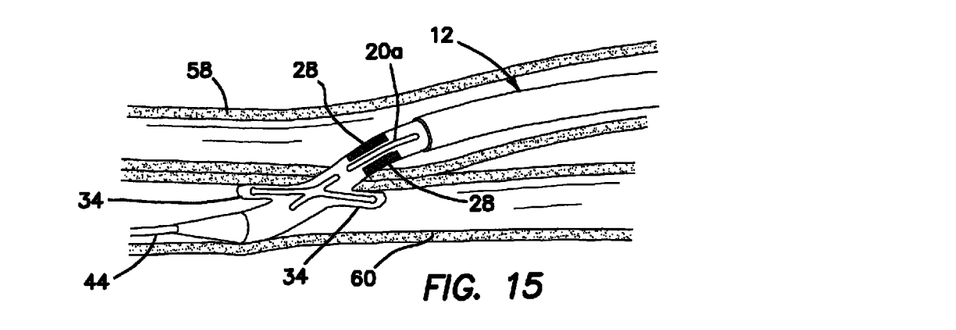

The outer tube or sheath 12 is retracted proximally to expose the underlying catheter, as shown in FIG. 13, sufficiently to expose the first pairs of opposed slots 20. The inner tube 16 (FIG. 20) is retracted by the activation lever 24 to first position 1, thereby causing the first pair of slots 20 to collapse and extend outwardly (FIG. 14). Once locked in place, the catheter is pulled back, causing the second vessel 60 to come into contact with the first vessel 58 (FIG. 15).

Figure 16:
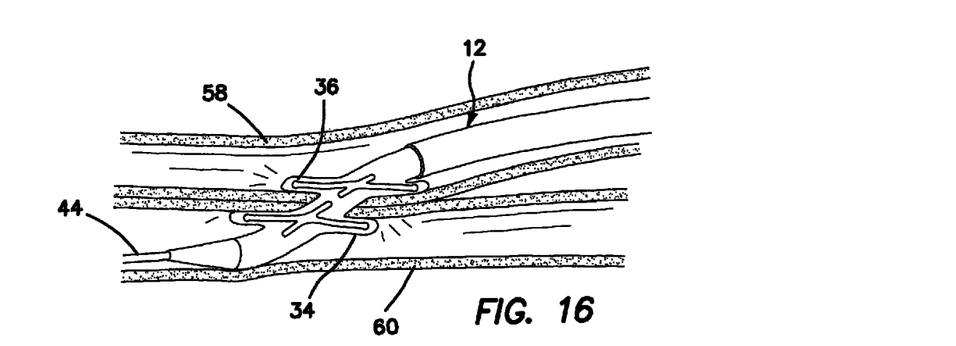
Figure 17:
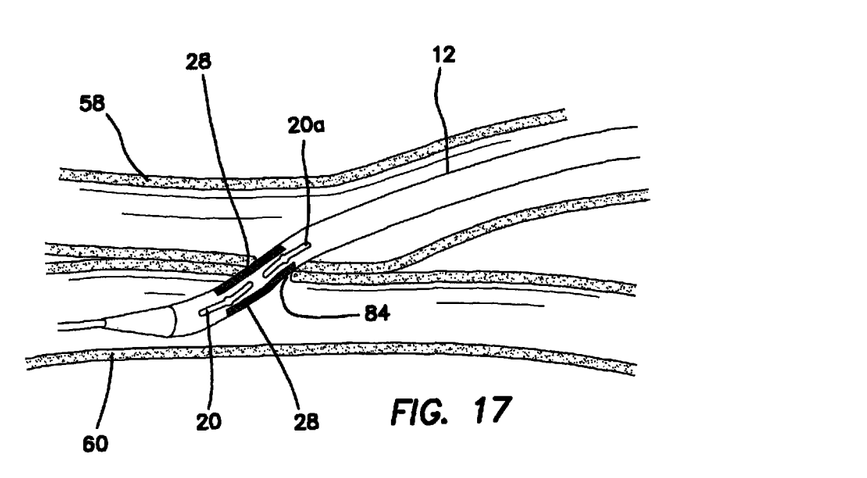
Figure 18:
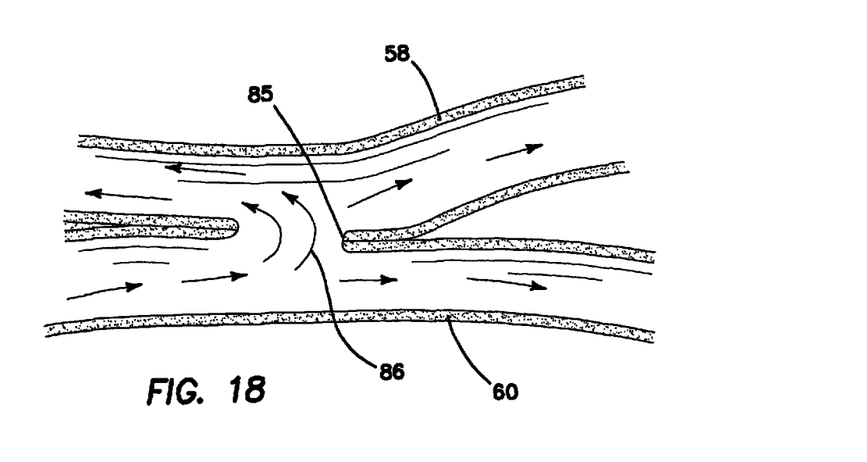

At this juncture, the outer sheath 12 is retracted further, to expose the second set of slots 20a (FIG. 16). The activation lever 24 is then retracted from the first position 31a to the second position 31b, which causes the second pair of slots 20a to collapse and extend outwardly, forming the second radially protruding wings 36, trapping the surrounding wall of the first vessel and second vessel between them (FIG. 16). RF energy is then applied, and the mesh electrodes 28 on both extended members create the weld between the first and second vessels. More particularly, the RF energy functions to burn and fuse or weld the vessels together, creating an elongate aperture 84 through the opposing walls of each of the first vessel 58 and second vessel 60, as well as any intervening tissue. This elongate aperture 84 is shown in FIGS. 17 and 18. Alternative cutting approaches, such as resistive heat (hot wire), ultrasonic, laser, or mechanical approaches, may be used instead of RF energy, if desired. The wings 34, 36 are then collapsed by returning the activation lever 24 back to its original position, and the catheter 12 is removed (FIG. 17).

As formed, the elongate aperture 84 will typically resemble a slit. However, as pressurized flow 86 (FIG. 18) begins to occur through the slit or aperture 84, which creates a communicating passage between the first vessel 58 and the second vessel 60, the aperture widens responsive to the pressure, taking the shape of an ellipse as it opens to form the desired fistula. The edges of the aperture are cauterized and welded.

Tissue welding of the type intended to occur in the practice of these inventive methods is discussed in U.S. Pat. No. 6,908,463, to Treat et al., which is herein expressly incorporated by reference, in its entirety.

Figures 21, 21A:
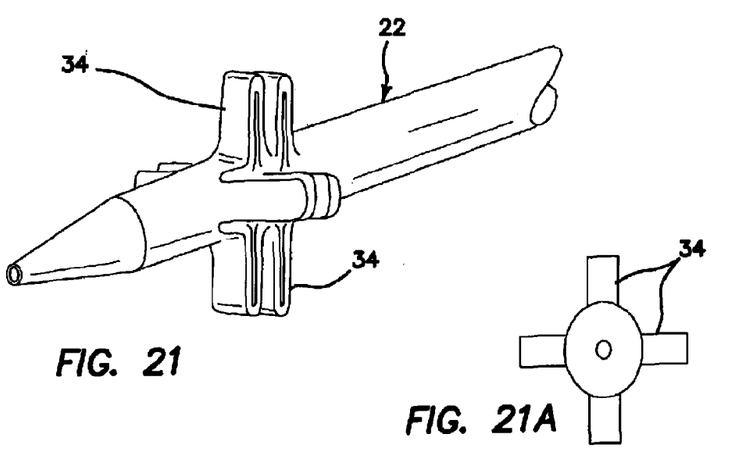
FIG. 21 is a view similar to FIG. 20b, showing an alternative embodiment.
FIG. 21a is an end view of the device shown in FIG. 21.
Figures 22, 22A:
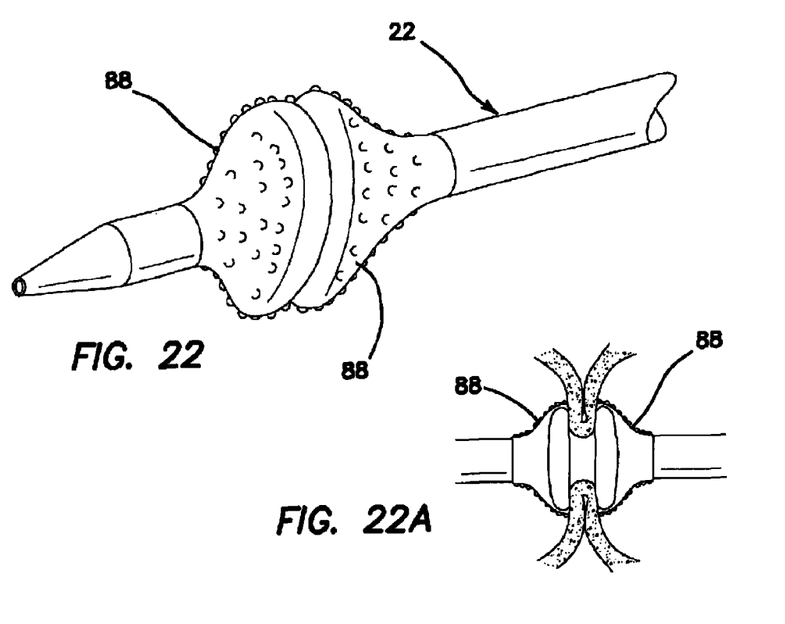
FIG. 22 is a view similar to FIG. 20b, illustrating another alternative embodiment.
FIG. 22a is an isolation view showing still another alternative embodiment.

FIGS. 21, 21a, 22, and 22a illustrate alternative configurations of the inventive device. In FIGS. 21 and 21a, multiple slots are illustrated for fainting multiple wings 34, which may be four, six, or eight. Coated wire expandable mesh tubing to form two conformable cones 88, with the internal facing surfaces exposed to create an electrode (FIG. 22). FIG. 22a illustrates that the RF energy source may also be bipolar, which localizes the heat and welded area.

In yet another unillustrated embodiment, two pair of opposable slits may be mounted on separate coaxial elongate bodies. The second coaxial body with a pair of collapsible slits allows for a predetermined force or pressure on the tissue that is to be welded. This force can be either by manual operator "feel" or by use of a spring or tensioning means. The spring tension can also be manually manipulated by rotating the housing, which will vary the compressive spring force, thus allowing the operator to "tune" the compression or force depending on the distance and composition of fat and tissue between the artery and vein.

In still another unillustrated embodiment, the slits on the coaxial bodies are positioned 90 degrees apart. This arrangement in a bipolar mode allows for the dispersion of energy equally around the circumference of the anastomosis thus creating a symmetrical weld. The slits on the first body will house the electrode for the first pole and the slits on the second body with house the electrode for the second pole.

In another embodiment, the second coaxial body is a coaxial tube with an circumferential electrode exposed only at the distal end.

Alternative configurations of the mounting of the electrodes on the collapsible slits are possible, wherein the electrodes are comprised of round or square stainless steel or nitinol wires in the range of 0.002-0.015 diameter communicated to the openings in the expanded slits through lumens in the elongate bodies. This configuration also allows for the electrodes to be in the bipolar configuration without having to be on separate coaxial bodies. A singe electrode may be exposed along the length of the expanded slit. Multiple parallel electrodes, may be utilized, wherein the electrodes are exposed as segmented parallel diameters. This configuration may also comprise staggered squares, rectangles or ovals, depending on the desired weld and associated vessels to be welded. Various electrode configurations can be attached at the proximal end and sequenced by use of a microprocessor or switching means. The electrodes are configured in opposable pairs to allow one pair to weld tissue until a predetermined resistance or impedance is recognized, the pair of electrodes will then shut off and the second pair is energized until the impedance or resistance level again reaches the predetermined amount and then this pair will shut off. This can be repeated for a multiple of electrodes. This will allow for controlled welding of the tissue and limit potential charring and necrosis at the weld site.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of creating an AV fistula between adjacent first and second blood vessels, comprising:
   cutting a hole through the adjacent walls of the first and second blood vessels by inserting a needle into the first blood vessel, extending an obturator cutting element through a lumen in the needle until a tip thereof contacts the wall of the first blood vessel, and energizing a cutting tip of the obturator to cut the hole;
   removing the obturator cutting element from the needle;
   inserting a guidewire through the needle lumen;
   inserting a welding catheter into the first vessel over the guidewire, and through the hole into the second vessel, so that a distal end of the welding catheter is disposed within the second vessel;
   expanding a first portion of wall defining the welding catheter radially outwardly;
   pulling the expanded first wall portion proximally to engage the wall of the second blood vessel and to pull it toward the wall of the first blood vessel;
   expanding a second portion of wall proximal to the expanded first wall portion and disposed in the first blood vessel radially outwardly, capturing the walls of each of the second and first blood vessels between the expanded first and second wall portions; and
   energizing cutting elements on said expanded first and second wall portions to create a tissue welded elongate aperture between the first and second blood vessels.

2. A method of creating an AV fistula between adjacent first and second blood vessels, comprising:
   cutting a hole through the adjacent walls of the first and second blood vessels;
   inserting a welding catheter into the first vessel, and through the hole into the second vessel, so that a distal end of the welding catheter is disposed within the second vessel;
   expanding a first portion of wall defining the welding catheter radially outwardly;
   pulling the expanded first wall portion proximally to engage the wall of the second blood vessel and to pull it toward the wall of the first blood vessel;
   expanding a second portion of wall proximal to the expanded first wall portion and disposed in the first blood vessel radially outwardly, capturing the walls of each of the second and first blood vessels between the expanded first and second wall portions; and
   energizing cutting elements on said expanded first and second wall portions to create a tissue welded elongate aperture between the first and second blood vessels;
   an outer sheath disposed over an elongate tube comprising the welding catheter, the method further comprising withdrawing the outer sheath proximally to expose the first wall portion prior to the first expanding step; and
   further withdrawing the outer sheath proximally to expose the second wall portion prior to the second expanding step.

3. The method as recited in claim 2, wherein the first wall portion comprises a plurality of circumferentially spaced slots disposed thereon, and the first wall portion expanding step comprises actuating the first wall portion to a collapsed orientation, wherein the plurality of circumferentially spaced slots and surrounding wall material are expanded radially outwardly.

4. The method as recited in claim 3, wherein the second wall portion comprises a second plurality of circumferentially spaced slots disposed thereon, and the second wall portion expanding step comprises actuating the second wall portion to a collapsed orientation, wherein the second plurality of circumferentially spaced slots and surrounding wall material are expanded radially outwardly.

5. A method of creating an AV fistula between adjacent first and second blood vessels, comprising:
- cutting a hole through the adjacent walls of the first and second blood vessels;
- inserting a welding catheter into the first vessel, and through the hole into the second vessel, so that a distal end of the welding catheter is disposed within the second vessel;
- expanding a first portion of wall defining the welding catheter radially outwardly;
- pulling the expanded first wall portion proximally to engage the wall of the second blood vessel and to pull it toward the wall of the first blood vessel;
- expanding a second portion of wall proximal to the expanded first wall portion and disposed in the first blood vessel radially outwardly, capturing the walls of each of the second and first blood vessels between the expanded first and second wall portions;
- energizing cutting elements on said expanded first and second wall portions to create a tissue welded elongate aperture between the first and second blood vessels;
- wherein the first wall portion comprises a plurality of circumferentially spaced slots disposed thereon, and the first wall portion expanding step comprises actuating the first wall portion to a collapsed orientation, wherein the plurality of circumferentially spaced slots and surrounding wall material are expanded radially outwardly; and
- wherein the second wall portion comprises a second plurality of circumferentially spaced slots disposed thereon, and the second wall portion expanding step comprises actuating the second wall portion to a collapsed orientation, wherein the second plurality of circumferentially spaced slots and surrounding wall material are expanded radially outwardly.

6. The method as recited in claim 1, wherein prior to the cutting step a first needle is advanced to puncture the first blood vessel.

7. The method as recited in claim 6, wherein the first needle is advanced into the first blood vessel.

8. The method as recited in claim 7, and further comprising advancing a first guidewire through a lumen in the first needle.

9. The method as recited in claim 8, and further comprising withdrawing the first needle from the first blood vessel, leaving the first guidewire within the first blood vessel.

10. The method as recited in claim 9, and further comprising advancing a vessel access catheter into the first blood vessel over the first guidewire, and advancing the vessel access catheter to a desired procedural site.

11. The method as recited in claim 1, wherein the first and second blood vessels comprise a vein and an artery.

12. The method as recited in claim 11, wherein the vein and the artery are disposed in a patient's hand.

13. The method as recited in claim 2, wherein the first and second blood vessels comprise a vein and an artery.

14. The method as recited in claim 13, wherein the vein and the artery are disposed in a patient's hand.

15. The method as recited in claim 5, wherein the first and second blood vessels comprise a vein and an artery.

16. The method as recited in claim 15, wherein the vein and the artery are disposed in a patient's hand.

* * * * *